United States Patent [19]
Mills et al.

[11] Patent Number: 5,447,509
[45] Date of Patent: Sep. 5, 1995

[54] ULTRASOUND CATHETER SYSTEM HAVING MODULATED OUTPUT WITH FEEDBACK CONTROL

[75] Inventors: Timothy C. Mills, Newport Beach; Henry Nita, Mission Viejo, both of Calif.

[73] Assignee: Baxter International Inc., Deerfield, Ill.

[21] Appl. No.: 131,796

[22] Filed: Oct. 4, 1993

Related U.S. Application Data

[60] Continuation-in-part of Ser. No. 94,416, Jul. 19, 1993, Pat. No. 5,397,301, which is a division of Ser. No. 640,190, Jan. 11, 1991, Pat. No. 5,304,115.

[51] Int. Cl.$^6$ .............................................. A61B 17/70
[52] U.S. Cl. ........................................ 606/1; 604/22; 128/662.03
[58] Field of Search ...................... 606/1, 2.5, 169–171; 607/97–99; 128/660.01–660.03, 662.03–662.06, 24, 44; 604/22; 601/2, 4

[56] References Cited

U.S. PATENT DOCUMENTS

| | | |
|---|---|---|
| 3,352,303 | 11/1967 | Delaney . |
| 3,433,226 | 3/1969 | Boyd . |
| 3,526,219 | 9/1970 | Balamuth . |
| 3,565,062 | 3/1971 | Kuris . |
| 3,589,363 | 6/1971 | Banko . |
| 3,618,594 | 11/1970 | Banko . |
| 3,809,093 | 5/1974 | Abraham . |
| 3,823,717 | 7/1974 | Pohlman . |
| 3,861,391 | 1/1975 | Antonevich et al. . |
| 4,188,952 | 2/1980 | Loschivlov et al. . |
| 4,214,586 | 7/1980 | Mericle . |
| 4,223,676 | 9/1980 | Wuchinich et al. . |
| 4,337,090 | 6/1982 | Harrison . |
| 4,366,819 | 1/1983 | Kaster . |
| 4,431,006 | 2/1984 | Trimmer et al. . |
| 4,474,180 | 10/1994 | Augulo . |
| 4,505,767 | 3/1985 | Quin . |
| 4,565,589 | 1/1986 | Harrison . |
| 4,587,958 | 5/1986 | Noguchi et al. . |
| 4,587,972 | 5/1986 | Morantte . |

(List continued on next page.)

FOREIGN PATENT DOCUMENTS

WO92/10140 6/1992 WIPO .

OTHER PUBLICATIONS

Circulation, vol. 81, No. 2, Feb. 1990, "Application of a New Phased-Array Ultrasound Imaging Catheter in the Assessment of Vascular Dimensions," pp. 660–666.
"Ultrasonic Energy Causes Doe-Dependent, Endothelium-Independent Arterial Relaxation"-T. Fischell, et al. Abstracts of the 63rd Scientific Sessions, p. lll–219.

Primary Examiner—Stephen C. Pellegrino
Assistant Examiner—Michael Peffley
Attorney, Agent, or Firm—Stetina Brunda & Buyan; Raymond Sun

[57] ABSTRACT

A method and apparatus for driving an ultrasound transducer coupled to an ultrasound transmission disposed within an elongate catheter has a modulated output and utilizes feedback control. A modulating signal varying in amplitude and continuous in duration modulates an ultrasound transducer drive signal. The resulting modulated ultrasound transducer drive signal is likewise continuous in duration such that it lacks the abrupt accelerations which cause stress to be applied to the ultrasound transmission member in prior art devices. The current of the modulated drive signal is monitored and the voltage thereof is varied in response to changes in the current in order to provide feedback control. A transmission member breakage alarm provides an indication of transmission member breakage in the event that any comparison of the drive energy to the feedback control signal indicates that the desired ultrasonic vibration has been reached at a drive energy level less than the minimum drive energy level typically desired for such desired ultrasound vibration when the ultrasound transmission member is intact.

19 Claims, 5 Drawing Sheets

U.S. PATENT DOCUMENTS

| | | |
|---|---|---|
| 4,589,419 | 5/1986 | Laughlin et al. . |
| 4,665,906 | 5/1987 | Jervis . |
| 4,692,139 | 9/1987 | Stiles . |
| 4,741,731 | 5/1988 | Starck . |
| 4,750,902 | 6/1988 | Wuchinich et al. . |
| 4,764,165 | 8/1988 | Reimels . |
| 4,794,931 | 1/1989 | Yock . |
| 4,799,496 | 1/1989 | Hargraves . |
| 4,800,876 | 1/1989 | Fox et al. . |
| 4,808,153 | 2/1989 | Parisi . |
| 4,811,743 | 3/1989 | Stevens . |
| 4,821,731 | 4/1989 | Martinelli . |
| 4,841,977 | 6/1989 | Griffith . |
| 4,844,092 | 7/1989 | Rydell . |
| 4,867,141 | 9/1989 | Nakada . |
| 4,870,953 | 10/1989 | DonMichael . |
| 4,896,811 | 1/1990 | Storz . |
| 4,898,575 | 2/1990 | Fischell et al. . |
| 4,917,097 | 4/1990 | Proudian et al. . |
| 4,919,133 | 4/1990 | Chiang . |
| 4,920,954 | 5/1990 | Alliger et al. . |
| 4,923,441 | 5/1990 | Shuler . |
| 4,924,864 | 5/1990 | Sterzer . |
| 4,936,281 | 6/1990 | Stasz . |
| 4,957,111 | 9/1990 | Millar . |
| 4,960,411 | 10/1990 | Buchbinder . |
| 4,966,583 | 10/1990 | Debbas . |
| 4,967,653 | 11/1990 | Hinz . |
| 4,967,753 | 11/1990 | Haase et al. . |
| 4,979,939 | 12/1990 | Shiber . |
| 4,988,356 | 1/1991 | Crittenden . |
| 4,989,583 | 2/1991 | Hood . |
| 4,998,527 | 3/1991 | Meyer . |
| 5,022,399 | 6/1991 | Biegeleisen . |
| 5,029,588 | 7/1991 | Yock et al. . |
| 5,058,570 | 10/1991 | Idemoto et al. . |
| 5,061,238 | 10/1991 | Shuler . |
| 5,069,664 | 12/1991 | Guess et al. . |
| 5,076,276 | 12/1991 | Sakurai et al. . |
| 5,100,423 | 3/1992 | Fearnot . |
| 5,151,085 | 9/1992 | Sakurai . |
| 5,163,421 | 11/1992 | Bernstein . |
| 5,188,589 | 2/1993 | Wypych . |
| 5,199,943 | 4/1993 | Wypych . |
| 5,211,625 | 5/1993 | Sakurai . |
| 5,242,385 | 9/1993 | Strukel . |
| 5,248,296 | 9/1993 | Alliger . |
| 5,255,669 | 10/1993 | Kubota . |
| 5,261,877 | 11/1993 | Fine . |
| 5,267,954 | 12/1993 | Nita . |
| 5,269,297 | 12/1993 | Weng . |
| 5,302,115 | 4/1994 | Pflueger et al. ............... 606/169 |
| 5,312,328 | 5/1994 | Nita . |
| 5,326,342 | 7/1994 | Pflueger . |

ULTRASOUND CATHETER SYSTEM HAVING MODULATED OUTPUT WITH FEEDBACK CONTROL

RELATED APPLICATION

This patent application is a continuation-in-part of U.S. patent application Ser. No. 08/094,416, filed Jul. 19, 1993, now U.S. Pat. No. 5,397,301, entitled ULTRASOUND ANGIOPLASTY DEVICE INCORPORATING AN ULTRASOUND TRANSMISSION MEMBER MADE AT LEAST PARTIALLY FROM A SUPERELASTIC METAL ALLOY, which is in turn a divisional of U.S. patent application Ser. No. 07/640,190, filed Jan. 11, 1991, now U.S. Pat. No. 5,304,115, entitled ULTRASOUND ANGIOPLASTY DEVICE INCORPORATING IMPROVED TRANSMISSION MEMBER AND ABLATION PROBE, the entire disclosures of such prior patent applications being hereby expressly incorporated herein by reference.

FIELD OF THE INVENTION

The present invention pertains generally to medical devices and more particularly to a method and device for generating ultrasonic energy and delivering said ultrasonic energy to a treatment location within a mammalian body.

BACKGROUND OF THE INVENTION

A number of ultrasonic devices have heretofore been proposed for use in ablating or removing obstructive material from blood vessels. Examples of devices which purportedly utilize ultrasonic energy, alone or in conjunction with other treatment modalities, to remove obstructions from blood vessels include those described in U.S. Pat. Nos. 3,433,226 (Boyd), 3,823,717 (Pohlman, et al.), 4,808,153 (Parisi), 4,936,281 (Stasz), 3,565,062 (Kuris), 4,924,863 (Sterzer), 4,870,953 (Don Michael, et al.), 4,920,954 (Alliger, et al.), and 5,100,423 (Fearnot) as well as other patent publications WO87-05739 (Cooper), WO89-06515 (Bernstein, et al.), WO90-0130 (Sonic Needle Corp.), EP316789 (Don Michael, et al.), DE3,821,836 (Schubert) and DE2,438,648 (Pohlman).

Ultrasound transmitting catheters have been utilized to successfully ablate various types of obstructions from blood vessels of humans and animals. Particular success has been observed in ablation of atherosclerotic plaque or thromboembolic obstructions from peripheral blood vessels such as the femoral arteries. Successful applications of ultrasonic energy to smaller blood vessels, such as the coronary arteries, necessitates the use of ultrasound transmitting catheters which are sufficiently small and flexible to permit transluminal advancement of such catheter through the tortuous vasculature of the aortic arch and coronary tree.

Additionally, ultrasound transmitting catheters may be utilized to deliver ultrasonic energy to blood vessel walls for purposes of preventing or reversing vasospasm as described in copending U.S. patent application Ser. No. 07/911,651, entitled ANGIOPLASTY AND ABLATIVE DEVICES HAVING ONBOARD ULTRASOUND COMPONENTS AND DEVICES AND METHODS FOR UTILIZING ULTRASOUND TO TREAT OR PREVENT VASOSPASM.

In utilizing ultrasound catheters which are of a significant length i.e., longer than approximately 50 cm, additional problems arise. The dissipation of heat generated by the ultrasound transmission member within a catheter is one particular concern. Although it is known to flush coolant, i.e., saline, through the catheter to aid in the dissipation of heat, such procedure is not always adequate.

Bends formed in the ultrasound catheter as it passes through various anatomical vessels of the human body exacerbate the problem of heat dissipation. Such bends provide points of frictional contact between the catheter and the ultrasound transmission member, thus resulting in excessive heat build-up.

As those skilled in the art will appreciate, the build-up of heat within the ultrasound catheter can result in damage to the catheter as well as ineffective operation thereof.

One solution for mitigating the effects of heat build-up within such ultrasound catheters in the prior art has been to pulse the ultrasonic transducer such that ultrasound is applied to the ultrasound transmission member only intermittently. Such devices typically utilize a duty cycle of approximately 30-50%. Thus, heat build-up ceases during the 70-50% off portion of the duty cycle when no ultrasound is being applied to the ultrasound transmission member, thus providing for cooling of the ultrasound catheter.

Those skilled in the art will appreciate that a one hundred per cent duty cycle is defined by an output signal which is not modulated. In applications where heat dissipation is not a problem, such a one hundred per cent duty cycle may be utilized.

However, the use of such pulsing techniques increases the probability of ultrasonic transmission member breakage due to the large acceleration gradients experienced during the abrupt on/off cycling of the ultrasound transducer. Such large acceleration gradients result in ultrasound operational frequencies in excess of 20 KHz being applied to the ultrasound transmission member. It is preferred that operation ultrasound frequencies be maintained at less than approximately 20 KHz so as to limit the large acceleration gradients associated with higher operational ultrasound frequencies.

Those skilled in the art will recognize that such large acceleration gradients are commonly associated with on/off cycling of oscillating mechanical systems and are due to the extremely short time duration over which the system changes from the rest state to the moving state and vice versa.

Additionally, such pulsed systems typically provide reduced ablation efficacy due to the lengthy, i.e., 70-50%, off portion of the duty cycle.

As such, it would be beneficial to provide an ultrasound catheter which is not subject to the problems of inadequate heat dissipation and ultrasound transmission member breakage due to on/off cycling.

Furthermore, contemporary ultrasound catheters are subject to providing ineffective ablation due to variations in the intensity of the ultrasound energy provided at the distal tip of the ultrasound transmission member. Such variations in the intensity of the ultrasound energy at the distal tip of the ultrasound transmission member reduce the efficacy of the ablation process by causing the ultrasound catheter to operate at a lower than desired level. That is, such variations in intensity cause the distal tip of the ultrasound transmission member to radiate less than the desired intensity of ultrasound energy, even though the ultrasound transmission member may be driven at or near its maximum safe level.

Such variations in the intensity of the ultrasound energy radiated at the distal end of the ultrasound transmission member are typically due to bends encountered in the tortuous vessels of the human anatomy, particularly when accessing small vessels such as the coronary artery from remote locations such as the femoral artery. During such procedures the ultrasound catheter is required to make several sharp bends. Such bends inherently result in a reduction in the intensity of the ultrasound energy transmitted through the ultrasound transmission member. This is thought to be due to radiation and reflection losses inherent in transmitting ultrasound energy through such a bent transmission member and also due to frictional engagement of the ultrasound transmission member with the catheter at the site of the bend.

As such, it would be beneficial to provide an ultrasound catheter which substantially overcomes the problem of inadequate ablation efficacy due to ineffective ultrasound energy transmission, i.e., loose mechanical connection and/or bends in the catheter's path.

SUMMARY OF THE INVENTION

In accordance with the present invention there is provided a method and apparatus for delivering ultrasonic energy through an elongate catheter to a location within a mammalian body which provides a modulated output to reduce heat build-up, but which modulated output does not contribute to premature failure of the ultrasound transmission member due to large acceleration gradients, but rather modulated by slow varying functions, including but not limited to sign functions, triangular functions, etc., and also which utilizes feedback control to mitigate the problem of inadequate ablation efficacy due to ineffective ultrasound transmission from the ultrasound transducer to the ablation site.

The method for providing the modulated ultrasound output comprises providing a modulating signal which varies in amplitude and is continuous in duration. The phrase "continuous in duration" as used herein is defined to mean not constantly cycling on and off as in the prior art pulsed ultrasound systems whose on-off cycling results in abrupt, extremely large or fast varying functions, but rather providing a constantly present (though varying) signal until the application of ultrasound is discontinued. The modulating signal is applied to an ultrasound transducer drive signal so as to modulate the ultrasound transducer drive signal. The resulting modulated ultrasound transducer drive signal is continuous in duration and, thus, substantially lacks the abrupt acceleration gradients which are known to cause stress to be applied to the ultrasound transmission member. Thus, the stress commonly associated with premature failure or breakage of the ultrasound transmission member is substantially mitigated by utilizing an ultrasound transducer drive signal which varies in amplitude and which is continuous in duration.

As in the prior art, modulation of the drive signal with an amplitude varying modulating signal reduces the quantity of heat generated by the ultrasound transmission member within the catheter by providing periods of low energy transmission during which the ultrasonic catheter is allowed to cool off. However, modulation of the drive signal with a continuous modulating signal in the present invention mitigates the probability of breaking the ultrasound transmission member due to high acceleration gradients, since such acceleration gradients, which are common in the prior art, do not occur in such continuous waveforms. The modulating signal may comprise a sign wave. Although the figures show the modulation signal as a signwave, such signal may alternatively comprise many other show, varying functions, other than sign waves.

The modulating signal is preferably an optimized function for a particular application. The modulating signal is preferably selectable from a plurality of different modulating signals, each of the different modulating signals being an optimized function for a particular application. Thus, the modulating signal is preferably optimized for at least one particular application such as the ablation of atherosclerotic plaque or the ablation of thrombotic matter.

Transducer feedback control is provided so as to optimize ablation efficiency by maintaining a defined level of ultrasound energy output at the tip of the ultrasonic catheter. The use of transducer feedback control thus results in more consistent plaque ablation performance, reduced stress on the catheter, and increase catheter and transducer life.

More consistent placque ablation performance is achieved since the ultrasound energy output at the tip of the ultrasound catheter is maintained at the desired level, rather than being reduced to a level which results in suboptimal performance due to sharp bends in the catheter and loose mechanical connections of the ultrasound transmission member.

Stress on the catheter is reduced since feedback control makes it possible to maintain a desired level of energy output at the tip of the ultrasonic catheter without requiring that the catheter be over driven in order to assure the delivery of adequate ultrasound energy at the tip thereof. Thus, the ultrasound catheter may typically be operated at a lower average level of ultrasound energy than would otherwise be feasible. Reducing the average level of the ultrasound energy transmitted through the ultrasound catheter inherently lowers the stress thereon and consequently increases the life thereof. Additionally, since the ultrasound transducer is driven at a lower level, its life is likewise increased.

Monitoring circuitry senses changes in the ultrasound transducer current level and adjusts the source voltage power supply so as to maintain the transducer current within a specified range. The ultrasound transducer current level is representative of the power delivered to the distal tip of the ultrasound transmission member. Thus, monitoring the level of the ultrasound transducer current provides a means for monitoring the power delivered at the distal tip of the ultrasound transmission member. Thus, when the monitoring circuitry detects a higher than specified transducer current, the monitoring circuitry reduces the output of the source voltage power supply so as to bring the current back down into the specified range.

In the preferred embodiment of the present invention, when the monitoring circuitry detects transducer current approaching a higher than specified current level and is thus close to limiting the output of the source voltage power supply, a status indicator, e.g., LED, changes state, preferably from blinking to solid green, so as to indicate that limiting of the source voltage power supply output is about to occur. And, thus, the system is delivering a signal which is resulting in the ultrasound output at the catheter tip.

Sensing of the transducer current is preferably accomplished via a sensing transformer intermediate the source voltage power supply and the piezo-ceramic elements of the ultrasound transducer. In the preferred embodiment of the present invention, the secondary of this sensing transformer supplies a signal to a peak detector through a half-wave rectifier and low pass filter. The resulting signal is fed to an error amplifier having a gain setting of approximately ten. The error amplifier is in communication with the pulse width modular, window comparators, level shifters and push-pull MOSFET stage. This train of circuitry adjusts the DC voltage supply downward until the error amplifier signal is minimized. Thus, the output of the ultrasound transducer is maintained within an established range, i.e., above a level of minimum efficacy and below an upper threshold beyond which operation is limited by protocol.

The front panel indicator of the transducer feedback control is connected to a comparator which is AND functioned with a square wave signal having a frequency of approximately 6 Hz. The comparator changes state when the system is within a pre-determined margin of controlling the DC source voltage. This margin is changeable depending upon the type of catheter being driven.

An apparatus for practicing the method of the present invention comprises a modulated ultrasound transducer drive signal generator for providing a modulated ultrasound transducer drive signal; feedback circuitry for sensing the level of the ultrasound drive signal and for increasing the voltage thereof in response to a decrease in the current thereof; an ultrasound transducer receiving the modulated ultrasound transducer drive signal and for providing an ultrasound output; and an ultrasound transmission member attached to the ultrasound transducer for transmitting ultrasound from the ultrasound transducer to an intracorporeal location where required for therapy.

As those skilled in the art will recognize, the catheter is generally comprised of a catheter sheath having a lumen formed therein and having an ultrasound transmission member extending longitudinally through the lumen thereof.

A method for detecting and indicating breakage of the ultrasound transmission member comprises the steps of measuring a feedback control signal representing the ultrasonic vibration at the distal-most extent of the ultrasound transmission member; defining the minimal drive energy typically required to obtain a desired induced feedback control signal when the ultrasound transmission member is unbroken; periodically or continually comparing the drive energy being delivered to the induced feedback control signal being received; and providing a breakage alarm in the event that any comparison of the drive signal to the induced feedback control signal indicates that the desired ultrasonic vibration has been reached at a drive energy less than the minimum drive energy level typically required for such desired ultrasound vibration when the ultrasound transmission member is intact.

Thus, by comparing the drive energy to the feedback control signal, it is possible to detect the occurrence of ultrasound transmission member breakage. This is possible because the drive energy required to obtain the desired induced feedback control signal is substantially different when the ultrasound transmission member is broken from the induced feedback control signal provided when the ultrasound transmission member is unbroken. It takes substantially more drive energy to obtain the desired induced feedback control signal when the ultrasound transmission member is unbroken than it does when the ultrasound transmission is broken since the unbroken ultrasound transmission member represents a greater load and thus requires more energy to drive.

The modulated ultrasound transducer drive signal generator comprises a modulating signal generator for providing a varying and continuous modulating signal; an ultrasound transducer drive signal generator for providing an ultrasound drive signal; and a modulator for applying the modulating signal to the drive signal so as to generate a modulated ultrasound transducer drive signal. A display is preferably provided for displaying information regarding the modulated ultrasound transducer drive signal. For example, such information may comprise peak ultrasound power, modulation functions (Dp/dt) power delivery duration, etc.

Thus, the method of the present invention may be used, for example, in treating intravascular blockage by positioning the distal end of the ultrasound transmission member within a lumen of a blood vessel and abutting the distal end of the ultrasound transmission member to the intravascular blockage. Modulation of the output of the ultrasound transducer mitigates heat build-up without subjecting the ultrasound transmission member to premature failure due to the effects of large acceleration gradients and feedback control mitigates the problem of inadequate ablation efficacy due to ineffective ultrasound energy transmission from ultrasound transducer to the ablation site. Those skilled in the art will recognize the various other intracorporeal applications of the present invention likewise exist.

These, as well as other advantages of the present invention will be more apparent from the following description and drawings. It is understood that changes in these specific structures shown and described may be made within the scope of the claims without departing from the spirit of the invention.

DETAILED DESCRIPTION OF THE PREFERRED EMBODIMENT

The detailed description set forth below in connection with the appended drawings is intended as a description of the presently preferred embodiment of the invention, and is not intended to represent the only form in which the present invention may be constructed or utilized. The description sets forth the functions and sequences of steps for constructing and operating the invention in connection with the illustrated embodiment. It is to be understood, however, that the same or equivalent functions and sequences may be accomplished by different embodiments that are also intended to be encompassed within the spirit and scope of the invention.

The method and apparatus for removing obstructions from anatomic structures of the present invention is illustrated in FIGS. 1 and 3-8 which depict a presently preferred embodiment of the invention. FIG. 2 depicts the wave forms of the transducer drive signal and modulating signal according to the prior art.

Figure 1:
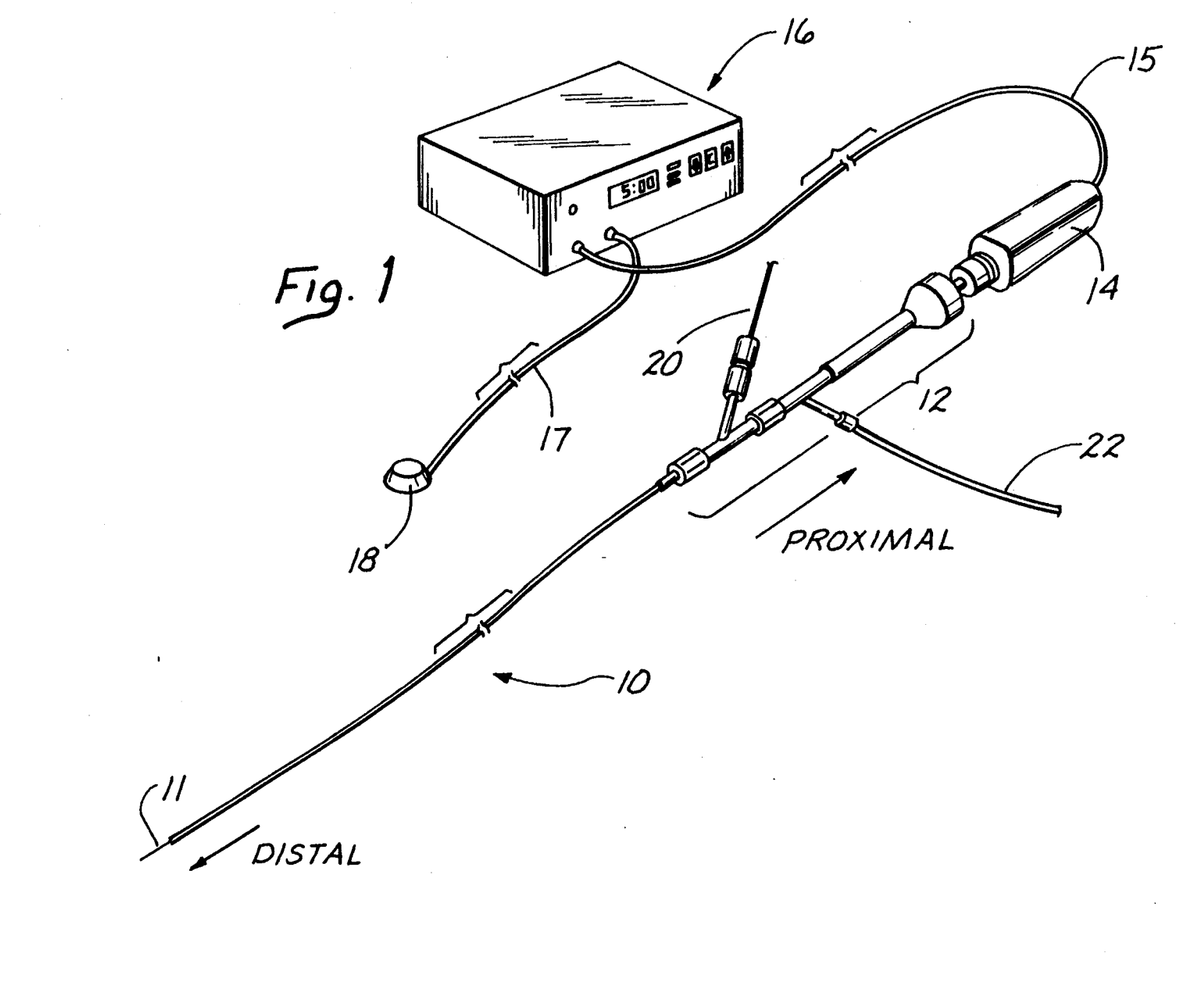
FIG. 1 is a perspective view of the ultrasound catheter system according to the present invention.
Figure 2:
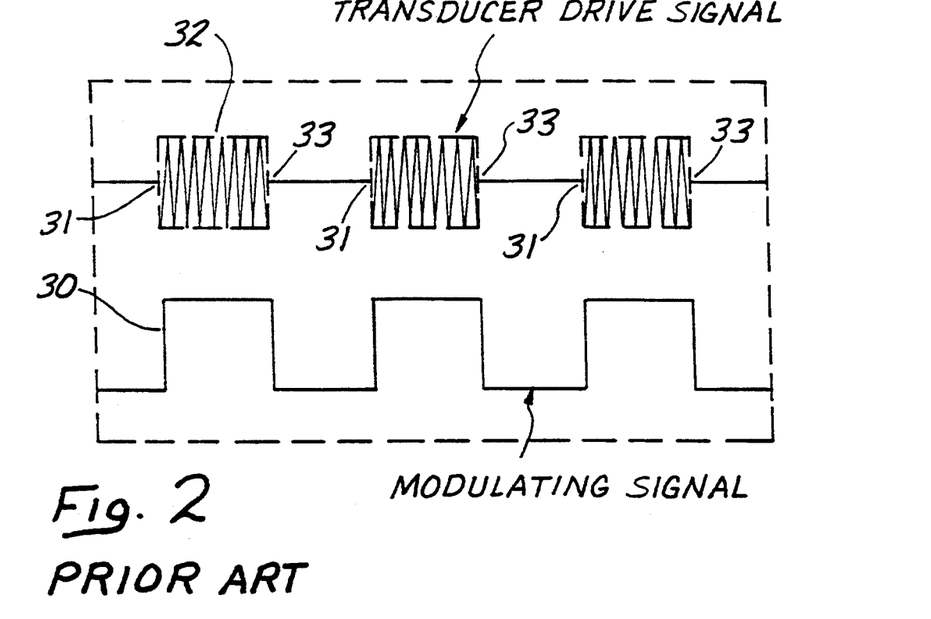
FIG. 2 is a graphic representation of the transducer drive signal and modulating signal according to the prior art.

Referring now to FIG. 1, an over-the-wire ultrasound catheter 10 having a proximal end connector assembly 12 mounted on the proximal end thereof is depicted. An ultrasound transducer 14 is connected to the proximal end of the proximal connector assembly 12. Ultrasound generator and control electronics 16 has a foot-actuated on/off switch 18 and is operatively connected to the ultrasound transducer 14 so as to send ultrasound energy through the ultrasound catheter 10, when desired.

An ultrasound transmission member 11 extends through the ultrasound catheter 10 such that the distal end thereof extends from the ultrasound catheter 10 so as to facilitate ablation of plaque, thrombosis, etc., and such that the proximal end thereof attaches to the ultrasound transducer 14.

First 20 and second 22 Y-connections facilitate the introduction of a saline solution for cooling the ultrasound catheter as well as the introduction of radiopaque dyes, anti-spasmodic medication, etc., as desired.

Contemporary ultrasound therapeutic medical devices typically deliver ultrasonic vibration at a frequency of 20-khz and provide either a continuous output at a constant amplitude or a pulsed output between an on state and off state, thus defining a duty cycle typically between 30-50%.

However, attempts to utilize such devices, particularly in percutaneous angioplasty or endovascular ablative procedures wherein the ultrasound delivery member is of significant length i.e., in excess of 50 cm and is exposed to bends, i.e., such as those associated with the tortuous vasculature of the aortic arch and coronary tree have encountered substantial problems. The use of ultrasound devices having a continuous output, i.e., a constant amplitude, for angioplasty procedures may exceed the heat dissipating ability of the ultrasound catheter, thus resulting in excessive heat build-up and consequent damage thereto.

Pulsed systems providing an output with alternating on and off periods of ultrasound energy delivery have been developed in an attempt to overcome the disadvantages associated with such thermal build-up in continuous mode ultrasonic catheters. However, such pulsed systems typically result in reduced ablation efficacy and, additionally, often result in premature breakage of the ultrasonic transmission member due to the large acceleration gradients created by the abrupt on/off cycling. Lower ablation efficiency results due to the decreased, i.e., 30-50%, duty cycle of such pulsed systems.

More particularly, reduced ablation efficacy results from the complete lack of ultrasonic energy provided during the off periods, during which no drive signal is applied to the ultrasound transducer. Thus, when utilizing a 50% duty cycle, for example, only one-half of the energy which would be provided with a 100% duty cycle is delivered to the distal end of the ultrasound transmission member.

The abrupt on/off cycling of such pulse systems results in increased acceleration gradients which stress the ultrasound transmission member, particularly at locations proximate the ultrasonic transducer. Thus, contemporary pulsed systems commonly experience breakage of the ultrasound transmission member at this location.

Referring now to FIG. 2, prior art pulsed ultrasonic catheters utilize a square wave modulating signal 30 which is used to modulate a continuous transducer drive signal so as to produce a transducer drive signal 32 which is, thus, pulsed in a complimentary manner. The pulsed transducer drive signal defines an output having full amplitude at times corresponding to the peaks of the square wave modulating signal and having zero output at times corresponding to the valleys of the square wave modulating signal.

As will be appreciated by those skilled in the art, the transition of the pulsed or modulated transducer drive signal from the off or no output state to the on state causes a very high acceleration gradient as the ultrasound transmission member moves from a rest position to movement and vice versa. Thus, the beginnings 31 and endings 33 of each pulse of the transducer drive signal result in high levels of stress being applied to the ultrasound transmission member.

Such high acceleration gradients subject the ultrasound transmission member 11 to forces which are frequently sufficient to result in damage thereto, i.e., breaking away of the distal portion of the ultrasound transmission member 11.

Figure 3:
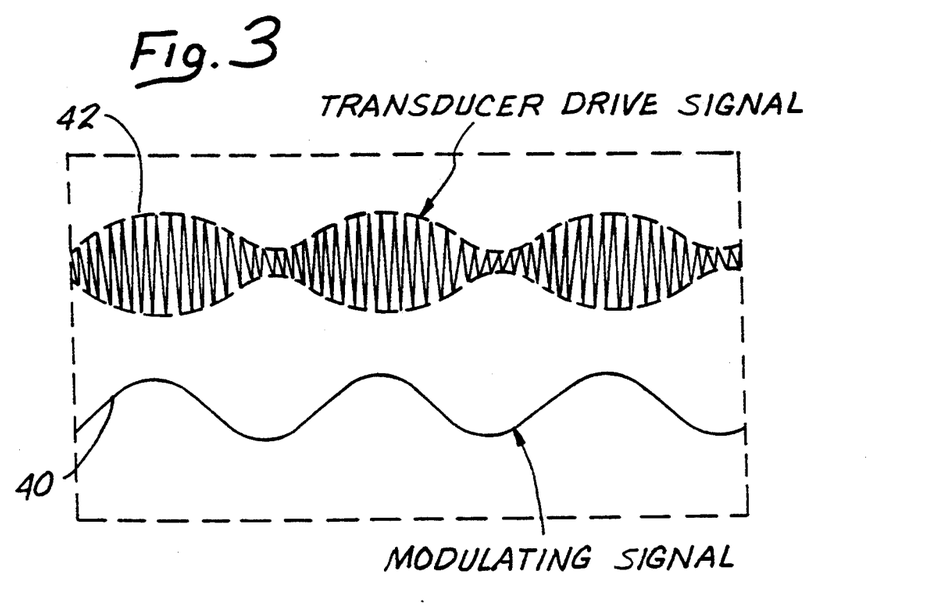
FIG. 3 is a graphic representation of one embodiment of the present invention which utilizes a sign wave function.

Referring now to FIG. 3, the modulating signal 40 of the present invention is a varying and continuous waveform, preferably a sine wave, which is used to modulate a continuous constant amplitude transducer drive signal so as to produce a modulated transducer drive signal 42 which is thus continuous and varying in amplitude. An effective duty cycle is achieved without actually allowing the ultrasound transmission member to come to a state of rest. Modulation of the transducer drive signal according to the present invention eliminates the need to induce the high acceleration gradients associated with bringing the ultrasound transmission member from a state of rest to one of motion and vice versa. Thus, those skilled in the art will appreciate that the stresses to which the ultrasound transmission member are exposed are substantially reduced.

Figure 4:
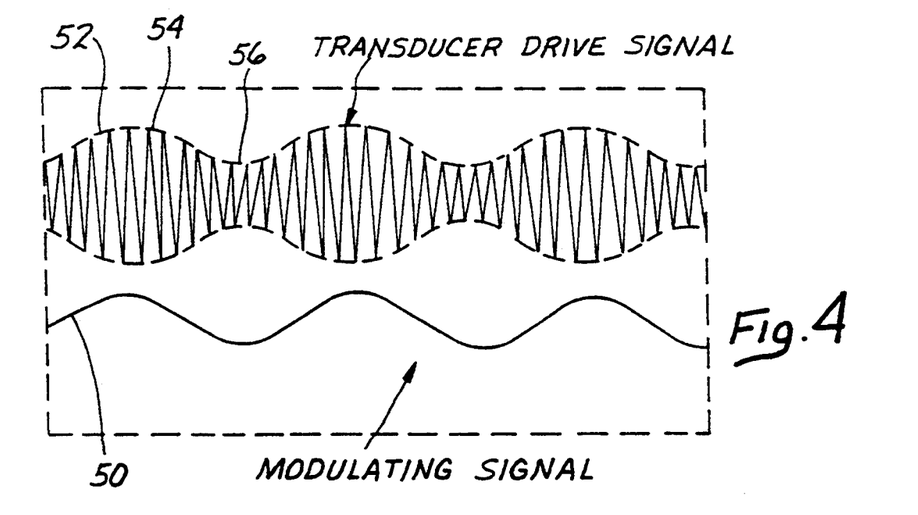
FIG. 4 is a graphic representation of the transducer drive signal and modulating signal according to the present invention wherein the amplitude of the modulating signal is increased, thus resulting in a corresponding increase in both the peaks and valleys of the modulated signal.
Figure 5:
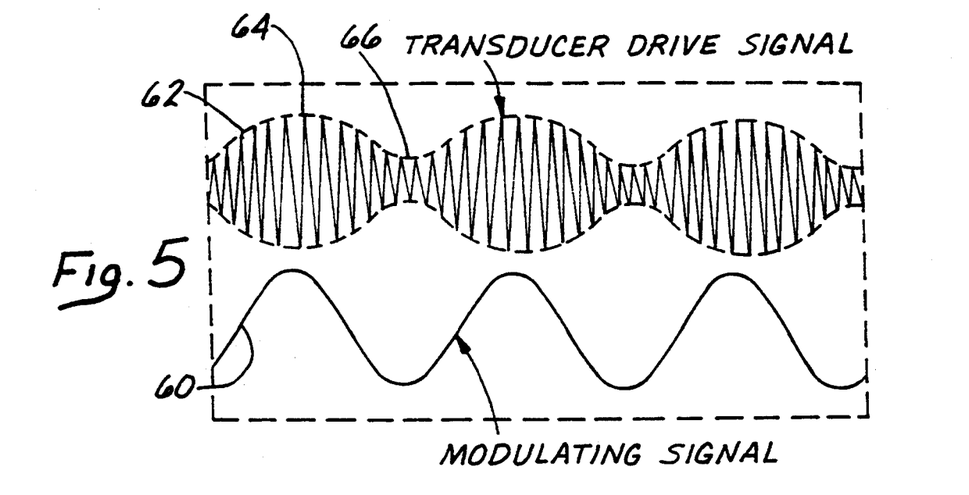
FIG. 5 is a graphic representation of the transducer drive signal and modulating signal according to the present invention wherein the amplitude of the modulating signal is increased, thus resulting in a corresponding increase in only the peaks of the modulated signal.

As shown in FIGS. 4 and 5, the modulation of the wave form brings about changes in the resultant effective duty cycle. For example, as the amplitude of the modulated signal is increased, the effective duty cycle is shortened. The effective duty cycle can thus be varied, as desired, by varying the amplitude of the modulating signal and the method of modulation.

Referring now to FIGS. 4 and 5, the effective duty cycle can be varied as a result of changes in the amplitude of the modulating signal.

Thus, increasing the amplitude of the modulating signal 40 of FIG. 3 may result in either increasing both the peaks 54 and valleys 56 of the transducer drive signal 52 as illustrated in FIG. 4 or and increasing only the peaks 64 (and not the valleys 66) of the transducer drive signal 62 as illustrated in FIG. 5.

Figure 6:
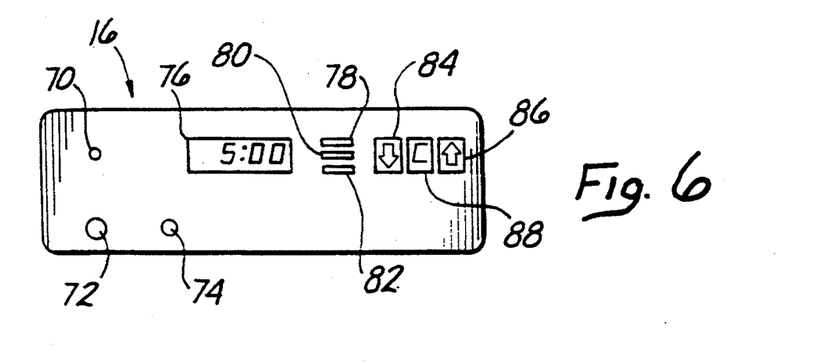
FIG. 6 is an enlarged front view of the control panel of the signal generation and control electronics of the ultrasound catheter of FIG. 1.

Referring now to FIG. 6, the controls and indicators of the signal generator and control electronics 16 are better illustrated. The front panel comprises a shut-down alarm indicator 70 which provides a visual indication that the ultrasound signal generator is not providing an output. Optionally, an audible enunciator may additionally be utilized to indicate shut-down of the system. A transducer connector 72 facilitates interconnection of the ultrasound signal generator and control electronics 16 and the ultrasound transducer 14 via interconnecting cable 15 (as shown in FIG. 1). A front panel jack 74 facilitates connection of the ultrasound signal generator and control electronics 16 with a foot switch 18 via cable 17 (as shown in FIG. 1), so as to facilitate remote operation of the ultrasound signal generator and control electronics 16.

Thus, the foot switch 18 may be utilized to control the application of ultrasound energy through the ultrasound transmission member 11 to the plaque or thrombosis, as desired.

Digital readout 76 indicates the remaining catheter lifetime. For example, contemporary protocol requires that ultrasound catheters be replaced after five(5) minutes of total use. Thus, by viewing digital readout 76, the user may readily ascertain the time remaining in the useful life of the ultrasound catheter.

For example, status indicator 78 may illuminate to indicate an operational condition of the ultrasound catheter. That is, status indicator 78 illuminates when ultrasound energy is being transmitted through the ultrasound transmission member 11.

As a further example, status indicator 80 may illuminate during the intermittent off-period of the ultrasound catheter 10. Contemporary protocol requires a five second off-period after each thirty seconds of ultrasonic energy applied.

As a still further example, status indicator 82 may illuminate to indicate that the catheter life has expired, i.e., five minutes of total time has accumulated during which ultrasound energy has been applied through the ultrasound transmission member 11.

Down 84 and up 86 membrane switches facilitate cycling between three different modes of operation. The selected mode of operation is indicated by digital indicator 88. Each time either the down 84 or the up 86 membrane switch is pushed, the selected mode of operation changes.

The irrigation mode is indicated by an "I" displayed in digital indicator 88. Cooling fluid, typically saline, is provided through ultrasound catheter 10 and no ultrasonic energy is applied when the irrigation mode is selected.

The peripheral mode is indicated by a "P" displayed in the digital indicator 88. When the peripheral mode of operation is selected, appropriate feedback control is maintained. Feedback control during peripheral mode operation may vary from that which is employed during coronary mode operation. Indeed, various different modes of operation may be selected wherein each different mode of operation corresponds to a different type of feedback control. Differences in feedback control may be provided to accommodate differences in catheter length, tip size, and power density required at the catheter tip.

The cardiac mode is indicated by a "C". Feedback control is provided so as to optimize ablation effectiveness while maintaining the ultrasound output level within protocol limits. The effects of sharp bends occurring in the tortuous path from the femoral artery to the coronary arteries, for example, are mitigated.

It will be recognized by those skilled in the art that the feedback control signal may comprise a variety of different signals generated by a variety of different means. For example, the feedback control signal may comprise the ultrasound transducer current level. Alternatively, the feedback control signal may comprise a signal generated by a vibration transducer mounted at the distal tip of the ultrasound catheter so as to directly measure ultrasonic vibration thereof.

Figure 7:
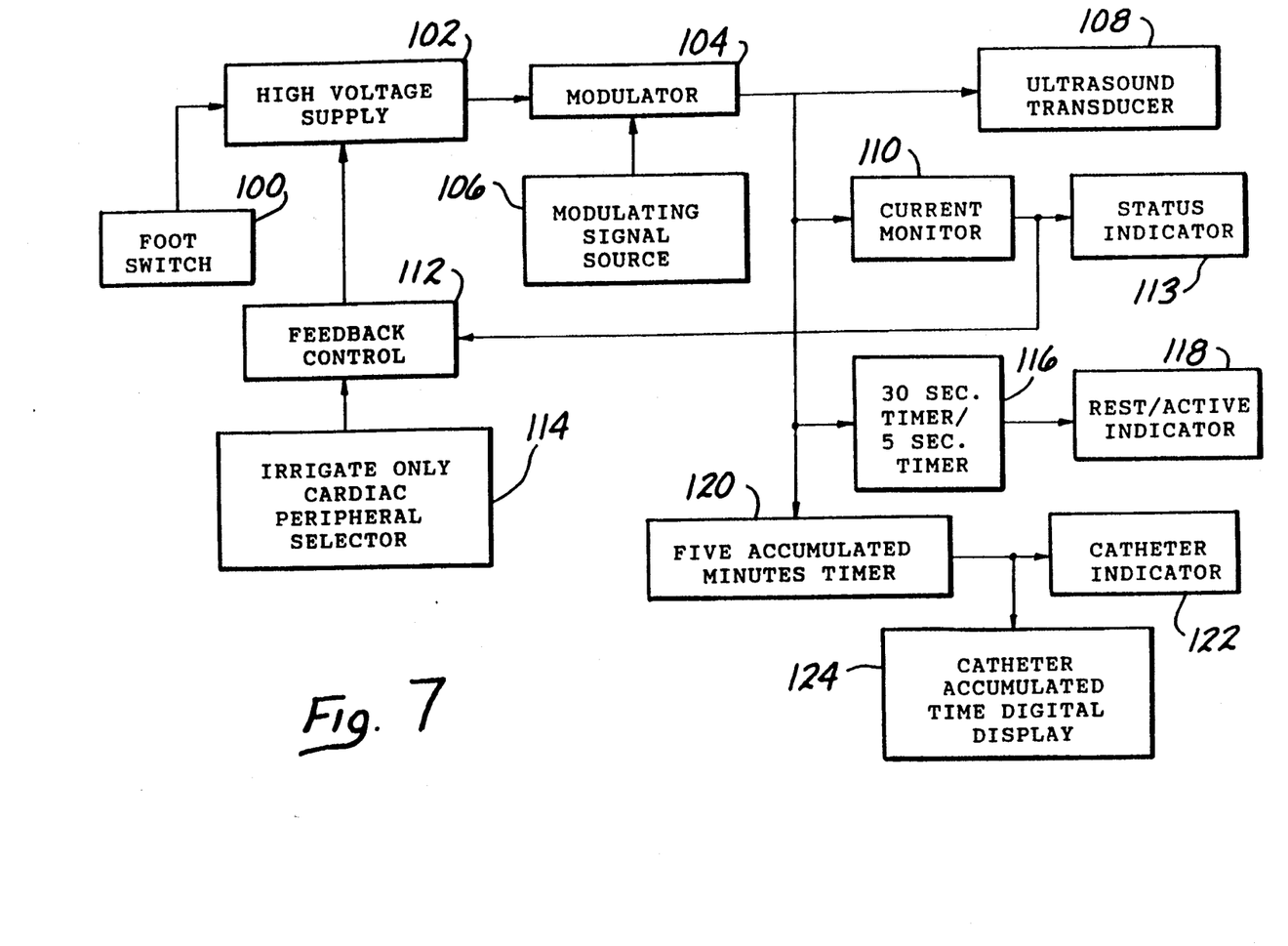
FIG. 7 is a block diagram of the signal generation and control electronics of the present invention illustrating those components utilized for feedback control and waveform modulation.

Referring now to FIG. 7, a block diagram of the signal generation and control electronics 16 is provided. A foot switch 100 controls the generation of an unmodulated transducer drive signal via the source voltage supply 102. The unmodulated transducer drive signal is provided by the source voltage supply 102 to a modulator 104. A modulating signal, preferably a sine wave, is provided by the modulating signal source 106 to the modulator 104 where modulation of the transducer drive signal is effected thereby. The modulator 104 provides a modulated transducer drive signal to the ultrasound transducer 108.

The current provided to the ultrasound transducer 108 is monitored by the current monitor 110, the output of which is used by the feedback control 112 to effect variations in the output of the source voltage supply 102, as required. Status indicator 113 (corresponding to status indicator 78 of FIG. 6) provides an indication of when feedback control is being utilized to effect changes in the output of the source voltage supply 102.

Sensing of the transducer current is preferably accomplished via a sensing transformer intermediate the source voltage power supply and the piezo-ceramic elements of the ultrasound transducer. In the preferred embodiment of the present invention, the secondary of this sensing transformer supplies a signal to a peak detector through a half-wave rectifier and low pass filter. The resulting signal is fed to an error amplifier having a gain setting of approximately ten. The error amplifier is in communication with the pulse width modular, window comparators, level shifters and push-pull MOSFET stage. This train of circuitry adjusts the DC voltage supply downward until the error amplifier signal is minimized. Thus, the output of the ultrasound transducer is maintained within an established range, i.e., above a level of minimum efficacy and below an upper threshold beyond which operation is limited by protocol.

The front panel indicator of the transducer feedback control is connected to a comparator which is AND functioned with a square wave signal having a frequency of approximately 6 Hz. The comparator changes state when the system is within a pre-determined margin of controlling the DC source voltage. This margin is changeable depending upon the type of catheter being driven.

The irrigate only/cardiac/peripheral selector 114 is utilized to select the desired mode of operation, i.e., irrigate only, cardiac, or peripheral.

Thirty-second timer/five-second timer 116 applies the output of the modulator 104 to the ultrasound transducer 108 according to contemporary protocol such that each thirty seconds of ultrasound energy applied through the ultrasound catheter 10 is followed by five seconds of off time. Rest/active indicator 118 (corresponding to status indicator 80 of FIG. 6) provides an indication of whether the ultrasound catheter is in the thirty-second on time or the five-second off period.

The five accumulated minutes timer 120 discontinues the application of ultrasound energy after five(5) minutes of total time have accumulated for a particular ultrasound catheter 10. The timer must be manually reset so as to confirm that the ultrasound catheter 10 has been replaced. Catheter indicator 122 (corresponding to status indicator 82 of FIG. 6) provides a quick visual indication of the status of the catheter, i.e., whether or not five(5) accumulated minutes have elapsed. The catheter accumulated time display 124 (corresponding to distal readout 76 of FIG. 6) provides a visual indication of the time remaining for operation of the ultrasound catheter 10.

The ultrasound transmission member breakage detector 109 provides a breakage alarm, either via status indicator 112 or via a separate dedicated alarm, in the event that any comparison of the drive energy to the induced feedback control signal indicates that the desired ultrasonic vibration has been reached at a drive energy level less than the minimum drive energy level typically required for such desired ultrasound vibration when the ultrasound transmission member is intact.

Figure 8:
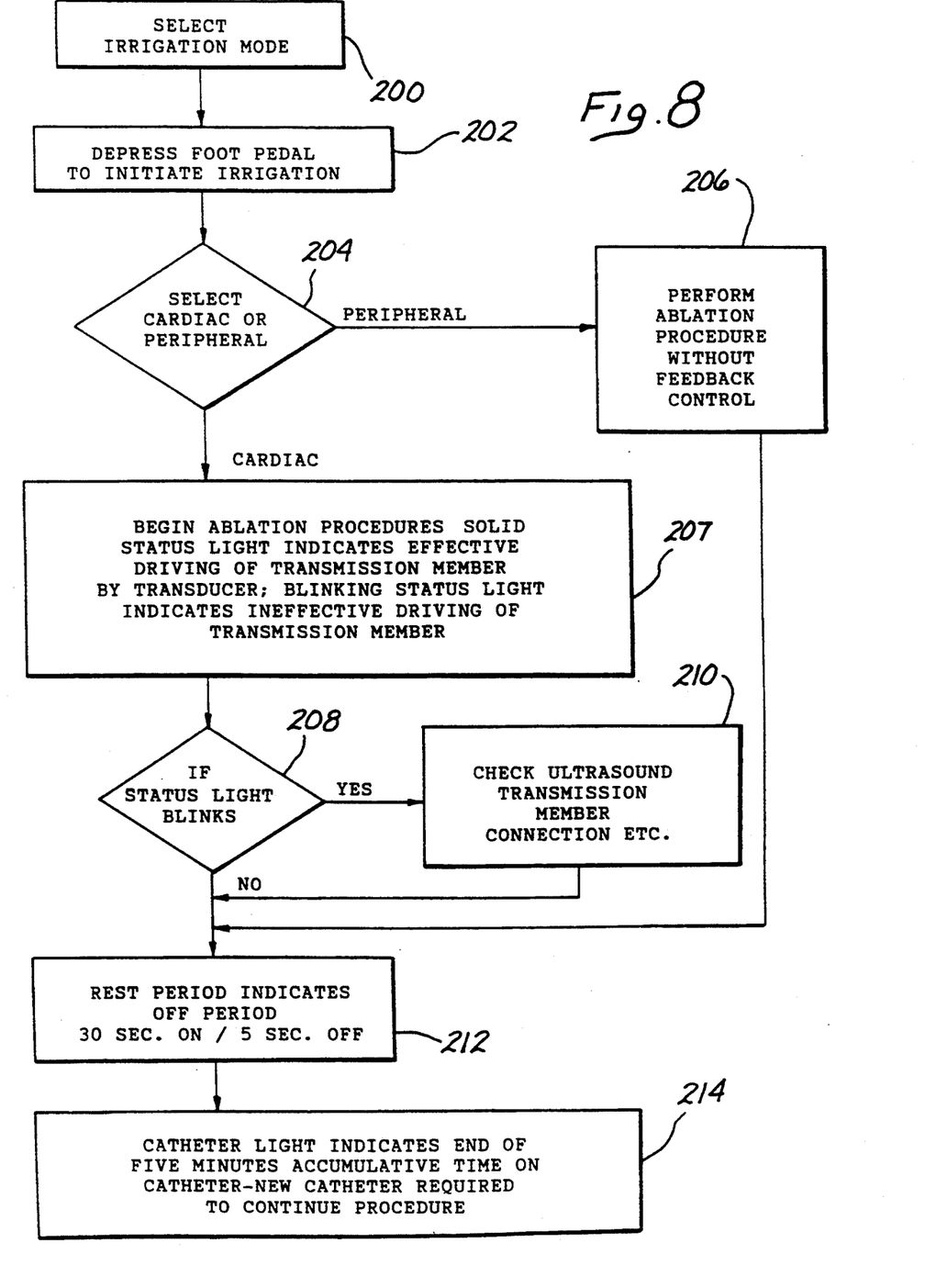
FIG. 8 is a functional block diagram illustrating the procedure utilized in the performance of ablation according to the present invention.

Now referring to FIG. 8, operation of the ultrasound catheter having modulated output with feedback control of the present invention is illustrated. The user first selects the irrigation mode 200, then depresses the foot pedal to initiate irrigation 202, as desired. Next, either the cardiac or peripheral mode of operation 204 is selected.

If the cardiac mode of operation is selected, the ablation procedure 207 is performed with feedback control. If the peripheral mode of operation is selected, then the ablation procedure is performed 206 with a different amount of total power delivered to the catheter and with different feedback control, if desired. A solid status light 78 (FIG. 6) indicates effective driving of the transmission member by the transducer and a blinking status light 78 indicates ineffective driving of the transmission member.

In either the peripheral or cardiac mode of operation, the output of the source voltage supply is modulated so as to facilitate adequate cooling of the ultrasound catheter 10 while minimizing stresses placed thereupon due to abrupt accelerations as occurs in the prior art.

If the status light 78 blinks 208 then the ultrasound transmission member may be checked for proper connection 210 and/or potentially manipulated so as to provide for the better transmission of ultrasound energy, i.e., by manipulating the ultrasound catheter so as to loosen any bends therein, where possible. As long as the status light does not blink 208, then the procedure proceeds according to protocol wherein thirty-seconds of operation are followed by five-seconds of off-time 212. If the status light continues to blink, such blinking may be an indication of a break or fracture of the transmission member and appropriate measures may be undertaken to replace the catheter before continuing.

Alternatively, a separate indicator may be provided to specifically indicate breakage of the ultrasound transmission member. Such breakage would be detected by sensing the presence of a desired feedback current when less than the normally required drive signal is provided.

The procedure may continue until the catheter life expired indicator 82 (FIG. 6) indicates that five minutes of total time have accumulated 214 on the catheter in use. The old catheter must be removed and a new catheter utilized prior to proceeding.

Thus, thermal build-up within the ultrasound catheter is controlled by optimizing the duty cycle of the transducer drive signal such that maximum ablation is achieved with acceptable thermal build-up.

Additionally, the wave form of the transducer drive signal can be optimized so as to provide effective ablation upon a wide range of body tissue, plaque, clots, thrombus, etc.

For example, a variety of different pre-programmed combinations of modulated signal function and source voltage amplitude may optionally be provided so as to optimize the application of ultrasound energy for a selected therapeutic function.

Breakage of the ultrasound transmission member may be optionally be detected. Differences in the feedback signal provided when the ultrasound catheter binds, i.e., due to excessive bending, and when the ultrasound transmission member fractures or is broken facilitate electronic differentiation between these two conditions. When the ultrasound transmission member binds, the feedback current decreases and in response to this decrease in the feedback current signal, the source voltage is increased. However, in the instance of ultrasound transmission member breakage, a normal feedback current signal is generated with the application of a substantially reduced source voltage. The normal feedback current signal results since it is possible to drive the shorter length of the broken ultrasound transmission member with less than the normally required source voltage. Detection of this condition makes it possible to indicate breakage of the ultrasound transmission member to the user so that the procedure may be halted and a new catheter provided.

Those skilled in the art will recognize that breakage of the ultrasound transmission member typically occurs within a few ultrasound modes of the ultrasound transducer, where ultrasound energy density concentration is the greatest. Thus, the difference in the source voltage required to drive a normal, i.e., unbroken, ultrasound transmission member and that required to drive a much shorter broken ultrasound transmission member is substantial.

It is understood that the exemplary method and apparatus for removing obstructions from anatomical structures described herein and shown in the drawings represents only a presently preferred embodiment of the invention. Indeed, various modifications and additions may be made to such embodiment without departing from the spirit and scope of the invention. For example the means for modulating the transducer drive signal with the modulating signal may comprise a variety type of circuits utilizing various solid state devices, vacuum tubes, and/or microprocessor means. Also, those skilled in the art will recognize that various thresholds for effecting changes in the output of the source voltage supply 102 in response to the input to the ultrasound transducer 108 are suitable, depending upon the physical characteristics of the ultrasound catheter, and the ultrasound energy requirements of the particular procedure being performed. Thus, these and other modifications and additions may be obvious to those skilled in the art and may be implemented to adapt the present invention for use in a variety of different applications.

What is claimed is:

1. A method for driving an ultrasound transducer coupled to an ultrasound catheter having an ultrasound transmission member extending longitudinally therethrough such that the distal end of the ultrasound transmission member oscillates at a desired operational ultrasound frequency, said method comprising the steps of:
   a) providing a modulating signal, the modulating signal varying in amplitude and being continuous in duration;
   b) applying said modulating signal to an ultrasound transducer drive signal so as to modulate the ultrasound transducer drive signal; and
   c) wherein the resulting modulated ultrasound transducer drive signal is continuous in duration and devoid of high frequency components which exceed the desired operational ultrasound frequency.

2. The method of claim 1 wherein the step of providing a modulating signal further comprises the step of providing a sine wave.

3. The method of claim 1 further comprising the steps of:
   a) monitoring the current of the modulated drive signal;
   b) varying the amplitude of the voltage of the modulated drive signal in response to changes in the current thereof; and
   c) wherein varying the amplitude of the voltage of the modulated drive signal in response to changes in the current thereof enhances ablation by reducing undesirable variations in ultrasound energy used therefor.

4. The method of claim 1 further comprising the step of selecting the modulating signal from a plurality of different modulating signals, each of the different modulating signals being an optimized function for a particular application.

5. The method as recited in claim 1 further comprising the steps of:
   a) measuring a feedback control signal representing the ultrasonic vibration at the distal-most extent of the ultrasound transmission member;
   b) defining the minimal drive energy typically required to obtain a desired induced feedback control signal when the ultrasound transmission member is unbroken;
   c) periodically or continually comparing the drive energy being delivered to the induced feedback control signal being received; and
   d) providing a breakage alarm in the event that any comparison of said drive energy to said induced feedback control signal indicates that said desired ultrasonic vibration has been reached at a drive energy level less than said minimum drive energy level typically required for such desired ultrasound vibration when said ultrasound transmission member is intact.

6. The method of claim 1, further comprising the step of optimizing said modulating signal for the ablation of atherosclerotic plaque.

7. The method of claim 1, further comprising the step of optimizing said modulating signal for the ablation of thrombotic matter.

8. A method for therapeutic treatment of a patient, said method comprising the steps of:
   a) positioning the distal end of an elongate ultrasound transmission member at a location within a mammalian body;
   b) applying a modulated electrical drive signal to an ultrasound transducer, the drive signal varying in amplitude and being continuous in duration; and
   c) transmitting the modulated ultrasound energy provided by the ultrasound transducer through an elongate ultrasound transmission member to a desired location within the mammalian body.

9. The method of claim 8 further comprising the step of disposing said ultrasound transmission member within a catheter sheath.

10. The method of claim 8 wherein the step of applying a modulated ultrasound transducer drive signal comprises modulating a constant amplitude ultrasound transducer drive signal with a varying and continuous modulating signal.

11. The method of claim 8 wherein the step of positioning the distal end of an ultrasound transmission member within a mammalian body comprises positioning the distal end of the ultrasound transmission member within a lumen of a blood vessel.

12. A method for driving an ultrasound transducer coupled to an ultrasound transmission member, the method comprising the steps of:
   a) providing an ultrasound transducer drive signal;
   b) monitoring the current of said ultrasound transducer drive signal; and
   c) varying the voltage of said ultrasound transducer drive signal in response to changes in the current thereof.

13. The method as recited in claim 12 further comprising the steps of:
   a) measuring a feedback control signal representing the ultrasonic vibration at the distal-most extent of the ultrasound transmission member;
   b) defining the minimal drive energy typically required to obtain a desired induced feedback control signal when the ultrasound transmission member is unbroken;
   c) periodically or continually comparing the drive energy being delivered to the induced feedback control signal being received; and
   d) providing a breakage alarm in the event that any comparison of said drive energy to said induced feedback control signal indicates that said desired ultrasonic vibration has been reached at a drive energy level less than said minimum drive energy level typically required for such desired ultrasound vibration when said ultrasound transmission member is intact.

14. An apparatus for providing ultrasound for use in therapeutic procedures, the apparatus comprising:
   a) a modulated ultrasound transducer drive signal generator for providing a continuous and varying modulated ultrasound transducer drive signal;
   b) an ultrasound transducer receiving said modulated ultrasound transducer drive signal and providing an ultrasound output; and
   c) an ultrasound transmission member having a distal tip, attached to said ultrasound transducer for transmitting ultrasound from said ultrasound transducer to an intracorporeal location where required for therapy.

15. The apparatus as recited in claim 14 further comprising a catheter substantially covering at least a portion of said ultrasound transmission member.

16. The apparatus as recited in claim 14 further comprising a display for displaying information regarding the modulated ultrasound transducer drive signal.

17. The apparatus as recited in claim 14 wherein said modulated ultrasound transducer drive signal generator comprises:
   a) a modulating signal generator for providing a varying and continuous modulating signal;
   b) an ultrasound transducer drive signal generator for providing an ultrasound drive signal; and
   c) a modulator for applying the modulating signal to the drive signal so as to generate a modulated ultrasound transducer drive signal.

18. The apparatus as recited in claim 17 further comprising:
   a) a current sensor coupled to the modulator for sensing current of the modulated ultrasound transducer drive signal; and
   b) a feedback control coupled to the current sensor and the ultrasound transducer drive signal generator for varying the voltage of the ultrasound transducer drive signal in response to changes in power delivered at the distal tip of the ultrasound transmission member.

19. In an ultrasonic system for ultrasonic ablation of matter within an anatomical structure of a mammalian body, said system comprising an ultrasound transducer coupled to an elongate ultrasound delivery catheter having an ultrasound transmitting member extending longitudinally therethrough, a method of detecting breakage of said ultrasound transmission member during use, said method comprising the steps of:
   a) measuring a feedback control signal representing the ultrasonic vibration at the distal-most extent of the ultrasound transmission member;
   b) defining the minimal drive energy typically required to obtain a desired induced feedback control signal when the ultrasound transmission member is unbroken;
   c) periodically. or continually comparing the drive energy being delivered to the induced feedback control signal being received; and
   d) providing a breakage alarm in the event that any comparison of said drive energy to said induced feedback control signal indicates that said desired ultrasonic vibration has been reached at a drive energy level less than said minimum drive energy level typically required for such desired ultrasound vibration when said ultrasound transmission member is intact.

* * * * *